United States Patent
Shinde et al.

(10) Patent No.: US 8,151,623 B2
(45) Date of Patent: Apr. 10, 2012

(54) SENSOR FOR QUANTIFYING WIDENING REDUCTION WEAR ON A SURFACE

(75) Inventors: Sachin R. Shinde, Oviedo, FL (US);
Anand A. Kulkarni, Oviedo, FL (US);
David J. Mitchell, Oviedo, FL (US);
Ramesh Subramanian, Oviedo, FL (US)

(73) Assignee: Siemens Energy, Inc., Orlando, FL (US)

( * ) Notice: Subject to any disclaimer, the term of this patent is extended or adjusted under 35 U.S.C. 154(b) by 414 days.

(21) Appl. No.: 12/469,988

(22) Filed: May 21, 2009

(65) Prior Publication Data
US 2009/0219040 A1  Sep. 3, 2009

Related U.S. Application Data

(63) Continuation-in-part of application No. 11/269,044, filed on Nov. 8, 2005, now Pat. No. 7,618,712, which is a continuation-in-part of application No. 11/122,566, filed on May 5, 2005, now abandoned, which is a continuation-in-part of application No. 11/018,816, filed on Dec. 20, 2004, now Pat. No. 7,270,890, which is a continuation-in-part of application No. 10/252,236, filed on Sep. 23, 2002, now Pat. No. 6,838,157.

(60) Provisional application No. 60/581,662, filed on Jun. 21, 2004.

(51) Int. Cl.
*G01N 3/56* (2006.01)
(52) U.S. Cl. .............................................. 73/7
(58) Field of Classification Search ........... 73/7, 776, 73/799, 802, 861, 775
See application file for complete search history.

(56) References Cited

U.S. PATENT DOCUMENTS

| | | | |
|---|---|---|---|
| 4,063,167 A | 12/1977 | Duly | |
| 4,253,913 A | 3/1981 | Chaudhuri | |
| 4,255,974 A | 3/1981 | Dufrane et al. | |
| 4,546,652 A * | 10/1985 | Virkar et al. ................ | 73/776 |
| 4,970,670 A | 11/1990 | Twerdochlib | |
| 5,119,036 A | 6/1992 | Rickards et al. | |
| 5,440,300 A | 8/1995 | Spillman, Jr. | |
| 5,760,593 A | 6/1998 | Lawrence et al. | |
| 5,797,414 A | 8/1998 | Sirovich et al. | |
| 5,867,302 A | 2/1999 | Fleming | |
| 5,952,836 A | 9/1999 | Haake | |
| 5,969,260 A | 10/1999 | Belk et al. | |
| 5,970,393 A | 10/1999 | Khorrami et al. | |
| 6,034,296 A | 3/2000 | Elvin et al. | |

(Continued)

FOREIGN PATENT DOCUMENTS

EP  0685297 A1  6/1995

(Continued)

*Primary Examiner* — Jewel V Thompson (57) ABSTRACT

A wear sensor (30, 50, 60) installed on a surface area (24) of a component (20, 21) subject to wear from an opposing surface (74, 75). The sensor has a proximal portion (32A, 52A, 62A) and a distal portion (32C, 52C, 62C) relative to a wear starting position (26). An electrical circuit (40) measures an electrical characteristic such as resistance of the sensor, which changes with progressive reduction of the sensor from the proximal portion to the distal portion during a widening reduction wear of the surface from the starting position. The measuring circuit quantifies the electrical changes to derive a wear depth based on a known geometry of the wear depth per wear width. In this manner, wear depth may be measured with a surface mounted sensor.

20 Claims, 6 Drawing Sheets

U.S. PATENT DOCUMENTS

| | | | |
|---|---|---|---|
| 6,043,644 | A | 3/2000 | de Coulon et al. |
| 6,109,783 | A | 8/2000 | Dobler et al. |
| 6,197,424 | B1 | 3/2001 | Morrison et al. |
| 6,251,488 | B1 | 6/2001 | Miller et al. |
| 6,262,550 | B1 | 7/2001 | Kliman et al. |
| 6,273,671 | B1 | 8/2001 | Ress, Jr. |
| 6,301,572 | B1 | 10/2001 | Harrison |
| 6,331,823 | B1 | 12/2001 | El-Ibiary |
| 6,343,251 | B1 | 1/2002 | Herron et al. |
| 6,512,379 | B2 | 1/2003 | Harrold et al. |
| 6,516,671 | B2 | 2/2003 | Romo et al. |
| 6,523,383 | B2 | 2/2003 | Joki et al. |
| 6,532,412 | B2 | 3/2003 | Adibhatla et al. |
| 6,556,956 | B1 | 4/2003 | Hunt |
| 6,576,861 | B2 | 6/2003 | Sampath et al. |
| 6,591,182 | B1 | 7/2003 | Cece et al. |
| 6,667,725 | B1 | 12/2003 | Simons et al. |
| 6,670,046 | B1 | 12/2003 | Xia |
| 6,717,420 | B2 | 4/2004 | Eyraud et al. |
| 6,723,379 | B2 | 4/2004 | Stark |
| 6,735,549 | B2 | 5/2004 | Ridolfo |
| 6,756,908 | B2 | 6/2004 | Gass et al. |
| 6,760,689 | B2 | 7/2004 | Follin et al. |
| 6,796,187 | B2 | 9/2004 | Srinivasan et al. |
| 6,816,817 | B1 | 11/2004 | Retlich et al. |
| 6,822,440 | B2 | 11/2004 | Machul |
| 6,831,555 | B1 | 12/2004 | Miller et al. |
| 6,838,157 | B2 | 1/2005 | Subramanian |
| 7,368,827 | B2 | 5/2008 | Kulkarni et al. |
| 2002/0170890 | A1 | 11/2002 | Keicher et al. |
| 2003/0122682 | A1* | 7/2003 | Gass et al. ............ 340/679 |
| 2006/0132149 | A1* | 6/2006 | Twerdochlib ............ 324/693 |

FOREIGN PATENT DOCUMENTS

| | | |
|---|---|---|
| EP | 1057586 A2 | 6/2000 |

* cited by examiner

SENSOR FOR QUANTIFYING WIDENING REDUCTION WEAR ON A SURFACE

CROSS REFERENCE TO RELATED APPLICATIONS

This application is a continuation-in-part of pending U.S. patent application Ser. No. 11/269,044 filed on Nov. 8, 2005 now U.S. Pat. No. 7,618,712, which is a continuation-in-part of pending U.S. patent application Ser. No. 11/122,566 filed May 5, 2005 now abandoned, which claims the benefit of Provisional Patent Application No. 60/581,662 filed on Jun. 21, 2004, and which is also a continuation-in-part of U.S. patent application Ser. No. 11/018,816 filed Dec. 20, 2004, now U.S. Pat. No. 7,270,890, which is a continuation-in-part of U.S. patent application Ser. No. 10/252,236 filed Sep. 23, 2002, now U.S. Pat. No. 6,838,157, all of which are incorporated herein by reference.

FIELD OF THE INVENTION

This invention relates to electrical sensors for detecting surface reduction wear as it widens and deepens on a surface, particularly wear on curved components such as spring clips in combustion turbine engines.

BACKGROUND OF THE INVENTION

Components such as spring clips in engines can experience surface wear from contact with other components under operational vibrations and dynamic forces. Sensors have been designed to provide real-time monitoring of component wear during engine operation. Such monitoring improves safety and reduces operating and maintenance costs by indicating a maintenance requirement before it causes damage or unscheduled outages.

It is known to place multiple sensors at different depths in a coating on a component surface to sense a depth of wear in real time. However, multi-layer sensors require significant extra work and expense to embed because each layer must be laid down separately. Generally, N sensors require about N times more work to install than 1 sensor. Also, placing sensors at multiple depths at a single location is problematic because sensor material is not a good wear material, so these sensors can cause spalling and can reduce the life of the wear material.

BRIEF DESCRIPTION OF THE DRAWINGS

The invention is explained in the following description in view of the drawings that show.

DETAILED DESCRIPTION OF THE INVENTION

Figures 1, 2:
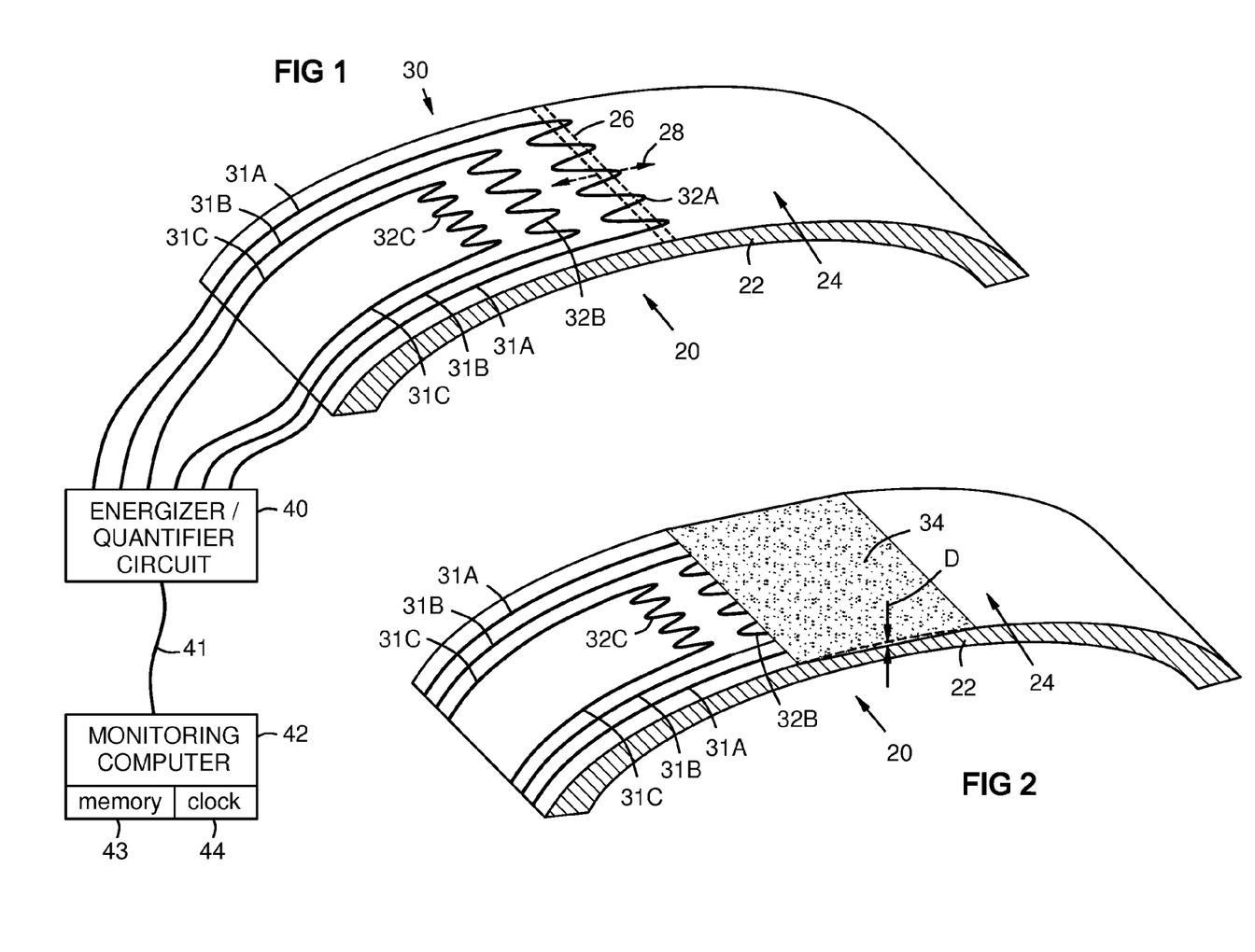
FIG. 1 is a perspective partial view of a curved component with a 2D sensor having three nested sub-elements.
FIG. 2 shows the component of FIG. 1 after wear from an opposed planar contacting surface.

FIG. 1 shows part of a component 20 having a substrate 22 with a surface 24. The surface 24 has a wear starting position 26, which is an initial contact area, point, or line of a touching component (not shown). The component 20 and the touching component have different curvatures. This results in a wear pattern that widens 28 predictably as it deepens. For example, the component 20 may be convex as shown, and the opposed component may be planar, or vice versa.

Figure 5:
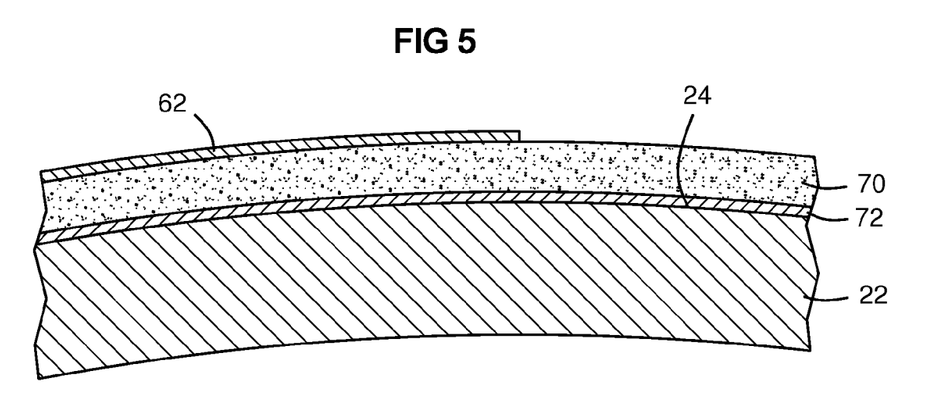
FIG. 5 is a sectional front view of a 2D sensor with film geometry installed on a coating on a component.
Figure 6:
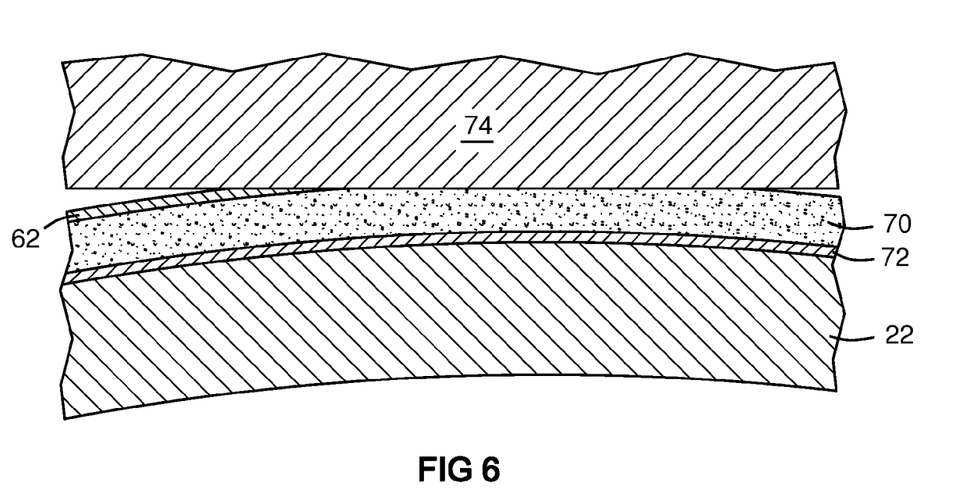
FIG. 6 shows a view as in FIG. 5 with an opposed planar component causing widening wear on the component and sensor.
Figure 7:
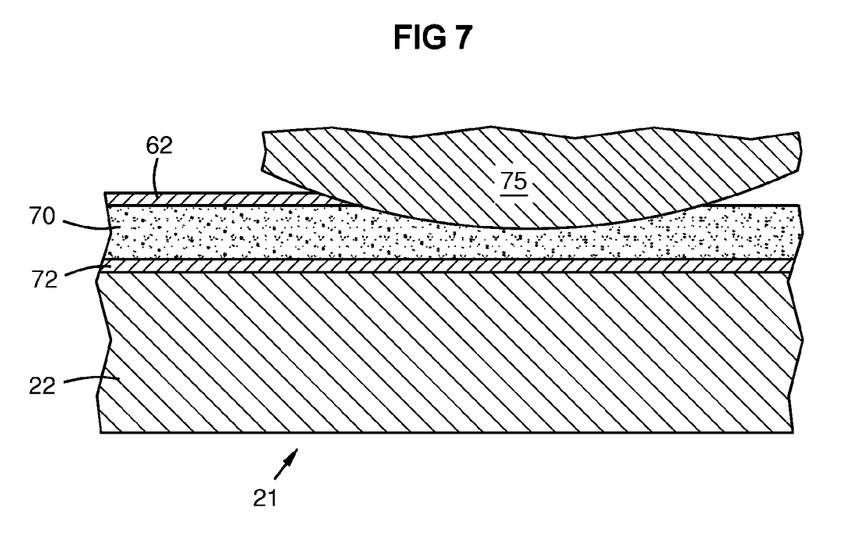
FIG. 7 is a sectional front view of a flat component and sensor being reduced by widening wear from an opposed curved component.
Figure 8:
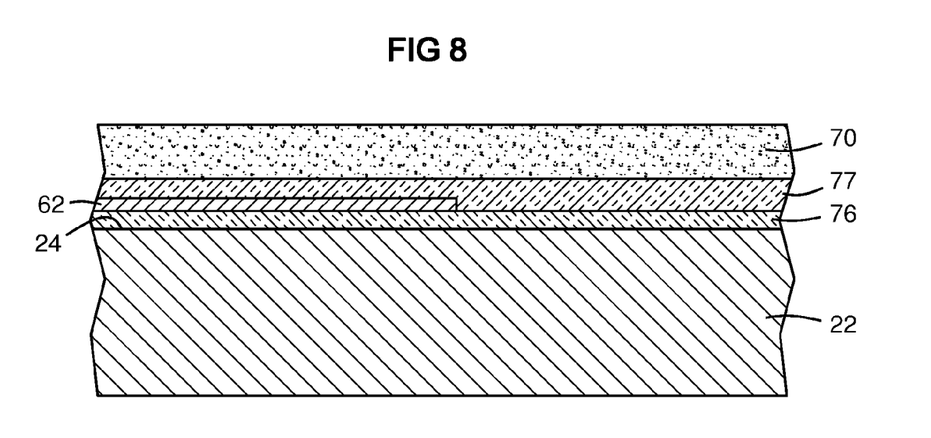
FIG. 8 is a sectional front view of a sensor installed between electrically insulating layers of a coating on a component.

A 2D sensor element 30 is installed on an area of the surface 24. Herein, the term "2D sensor element" means an element that follows a surface geometry at a single level. This definition includes for example a single wire, plural wires, a film, a ladder, and the like, that follows either a planar surface or a curved surface at a single level. The single level may be an outer uncoated surface as shown in FIGS. 1-4, an outer coated surface as shown in FIGS. 5-7, o a subsurface level with a further outer coating as shown in FIG. 8. Examples of curved surfaces include cylindrical and spherical surfaces. In contrast, a "3D sensor element" has features that are distinct at different depths in a surface or coating.

The 2D sensor element 30 in this embodiment comprises nested electrical conductor loops in the form of rail pairs 31A, 31B, 31C and respective rungs 32A, 32B, 32C. The 2D sensor includes a proximal portion 32A and a distal portion 32C relative to the wear starting position 26. Each rung in this embodiment may be independently connected to an electrical measuring circuit 40 that measures an electrical characteristic such as resistance, capacitance or impedance of each loop, and may also energize each loop. This circuit may include an analog to digital signal converter as known in the art. The electrical measuring circuit may be connected 41 to, or be a part of, a monitoring computer 42, which may include a memory 43 and a clock 44. In this example each nested loop comprises a zigzag rung between two rails. Zigzag rungs are not essential, but they may increase the sensitivity and/or coverage of each loop compared to alternates such as smoothly curved conductor loops or straight rungs.

The sensor elements of embodiments herein may be deposited on a substrate or within or on a wear-resistant layer such as a metal, ceramic, or cermet coating on a substrate as variously shown, using a thin film deposition process such as plasma spraying, electron beam physical vapor deposition, chemical vapor deposition, pulsed laser deposition, miniplasma, cold spray, direct-write, mini high velocity oxy-fuel, or solution plasma spraying, for example. The substrate may be metal or another material such as a ceramic or ceramic matrix composite. An appropriate deposition process may be selected accordingly as known in the art.

FIG. 2 shows a wear pattern 34 that has been worn to a given depth D by an opposed planar surface. The wear pattern 34 has a predictable growth geometry over time, based on the relative curvatures of the component surface 24 and the opposed surface. The proximal rung 32A and the middle rung 32B of the sensor element 30 have been broken in FIG. 2. The monitoring computer 42 can compute the wear depth D based on the width of the wear pattern 34 relative to its depth when a given rung is broken. Wear can be quantified as a percentage of maximum acceptable wear or in other units, such as age codes or numeric levels progressing from minor wear to maximum wear, as each successive rung 32A-C is broken.

Figure 3:
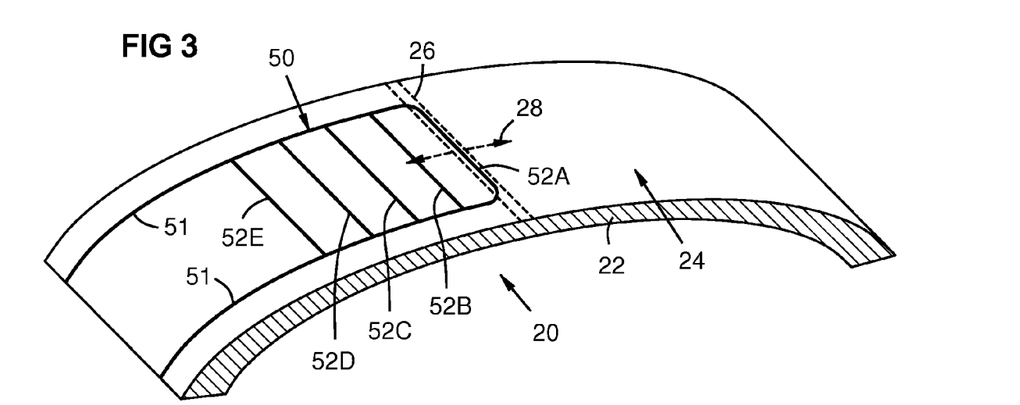
FIG. 3 shows a 2D sensor embodiment with a ladder geometry.

FIG. 3 shows a sensor embodiment 50 with a ladder geometry, including two generally parallel rails 51 and multiple rungs 52A-52E connected between the rails. This sensor produces stepwise changes in the characteristic measurement, which is shown as resistance in the embodiment of FIG. 10. These steps are detectable by the electrical measuring circuit 40, and allow it to quantify the depth of the wear using only a surface-mounted sensor.

Figure 4:
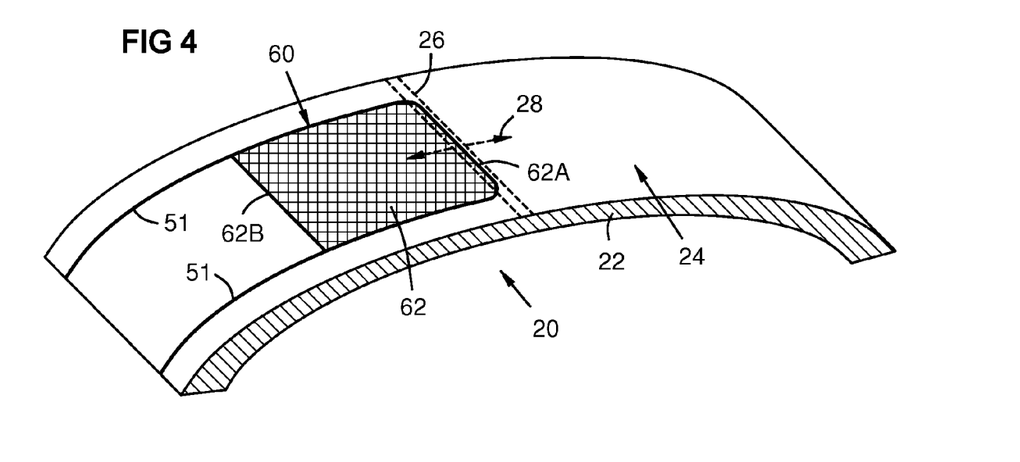
FIG. 4 shows a 2D sensor embodiment with a film geometry.
Figure 11:
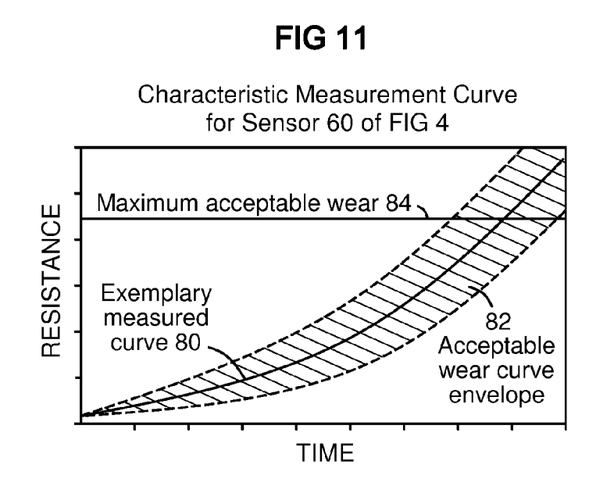
FIG. 11 shows a conceptual graph of characteristic measurement data from the sensor geometry of FIG. 4, and an acceptable time series envelope.

FIG. 4 shows a sensor embodiment 60 with a film geometry 62, including a proximal end 62A and a distal end 62B relative to the wear starting position 26. This sensor produces generally gradual changes in the characteristic measurement, as shown in FIG. 11. The electrical measuring circuit 40 quantifies the wear based on these changes.

FIG. 5 shows a sectional front view of a component with a sensor element 62 installed on a coating 70 on the substrate 22. The coating 70 may be a wear coating, an electrical insulation coating, or a thermal insulation coating over an optional bond coat 72 on the substrate 22 as known in the art.

FIG. 6 shows a view as in FIG. 5 with an opposed planar surface 74 causing wear on the coating and sensor. The film 62 has been reduced by this wear, resulting in a changed electrical characteristic of a circuit that includes sensor element 62.

FIG. 7 shows a sectional front view of a flat component 21 with a sensor element 62 being reduced by wear from an opposed curved surface 75.

FIG. 8 shows a sectional front view of a sensor element 62 installed between electrically insulating layers 76, 77 within a coating 70 on a component.

The sensor embodiments herein may be formed as follows:
1. If the substrate has a high dielectric constant, as with an insulating ceramic like $Al_2O_3$, the sensor element may be deposited directly on the substrate. Otherwise, deposit an electrically insulating layer 76 on the substrate surface 24 using a material such as an oxide ceramic with high dielectric/insulating properties like $Al_2O_3$, Yttria Stabilized Zirconia, and $MgAl_2O_4$.
2. Deposit the sensor layer 62 using an electrically conducting material with oxidation resistance at the operational temperature. For example Ni—Cr is suitable for operation at about 500° F. (260° C.), which works for a gas turbine combustor spring clip operating in this range. An exemplary sensor thickness is in the range of about 5-25 microns, with 5 microns being one embodiment.
3. If an electrically conductive wear coating is to be applied over the sensor, then first deposit an electrically insulating layer 77 over the sensor using an insulating material such as described in step 1. Such insulating layer 77 may be applied over the sensor without a further wear coating.
4. Optionally deposit a wear coating 70, such as an alloy of $Cr_2C_3$—NiCr or WC—Co, or commercial products known as Stellite 6B or T800. An exemplary thickness of the wear coating is in the range of about 0.4-0.5 mm.

Optionally, a trench or depression may be cut into the substrate for a sensor element, then the trench bottom surface may be coated with electrical insulation, then the sensor element may be deposited on the electrical insulation, then the sensor element may be coated with electrical insulation, then the trench may be filled with a wear resistant material or with the substrate material to achieve a smooth contact surface.

Figure 9:
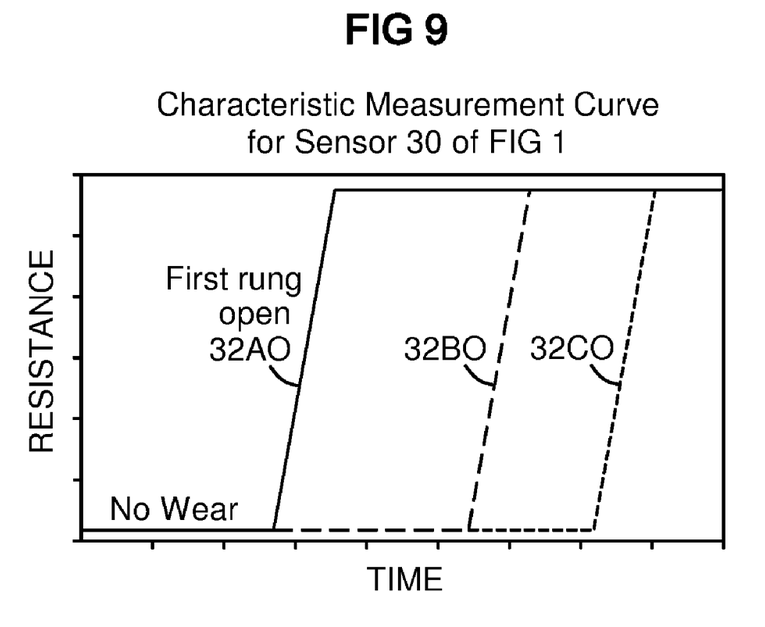
FIG. 9 shows a conceptual graph of characteristic measurement data from the sensor geometry of FIG. 1.

FIG. 9 shows a conceptual graph of characteristic measurement data from the sensor 30 of FIG. 1. As each rung 32A, 32B, 32C is successively broken by wear, a respective resistance measurement 32AO, 32BO, 32CO between respective rail pairs 31A, 31B, 31C jumps from low to high resistance.

Figure 10:
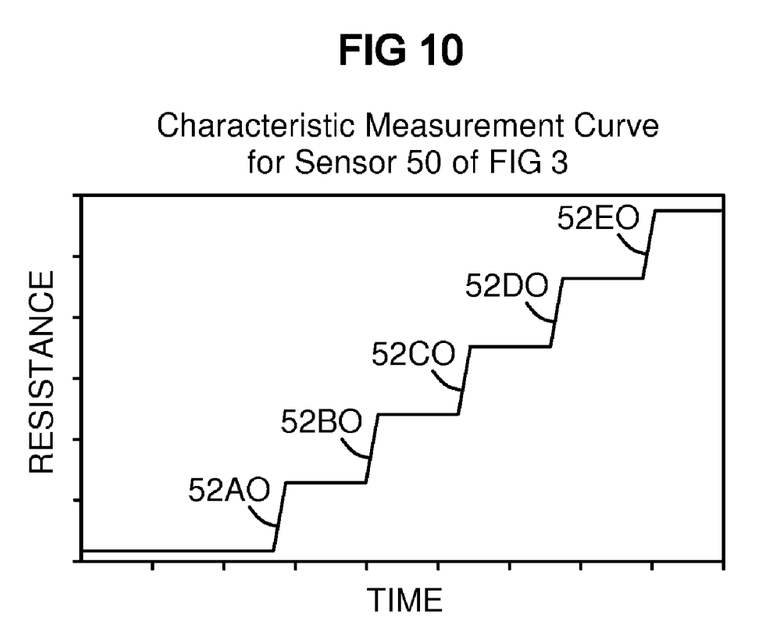
FIG. 10 shows a conceptual graph of characteristic measurement data from the sensor geometry of FIG. 3.

FIG. 10 shows a conceptual graph of characteristic measurement data from the sensor 50 of FIG. 3. As each rung 52A-52E is successively broken by wear, a respective step 52AO-52EO occurs in the resistance measurement of the sensor.

FIG. 11 shows a conceptual graph of characteristic measurement data from the sensor 60 of FIG. 4. Also illustrated is an acceptable wear envelope 84 for the measurement data curve 80. When a maximum wear limit 84 is reached, maintenance is required. The monitoring computer 40 may predict when this limit will be reached based on the slope of the measured data curve, and can thus provide a maintenance alert with a predetermined lead time.

Figure 12:
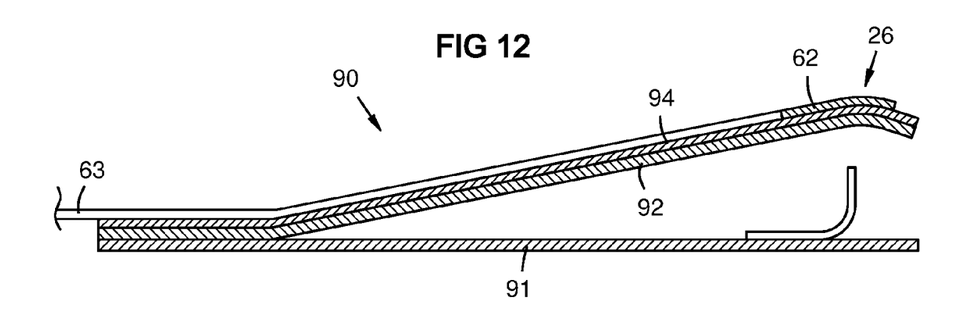
FIG. 12 shows a sensor installed on a gas turbine combustor spring clip.

FIG. 12 illustrates a sensor herein applied to a gas turbine combustor spring clip 90 having a base 91, a spring plate 92 with a curved wear starting position 26, an electrical insulation layer 94, a sensor element 62, and a sensor lead 63.

The monitoring computer 42 may store a time series of actual measured data 80 from each sensor, starting from an installation or replacement time of the sensor. Engineering data may be stored in the computer to provide an acceptable time series envelope 82 for the measured data. If a sensor does not measure an expected amount of wear after a given time interval, this may indicate a failed sensor, a bad connection, a loose component, or a manufacturing inconsistency. The clock may be configured to count operating time, real time, on-off cycles, and/or thermal cycles.

Each sensor 30, 50, 60 may have a proximal portion 32A, 52A, 62A that touches or crosses the wear starting position 26 as variously shown. Such a sensor will indicate even a slight amount of wear of the surface, which can provide early validation of the sensor and component. The computer may issue an alert if an actual measurement of the electrical characteristic over time is not within the acceptable time series envelope, indicating that the sensor is changing substantially faster or slower than expected.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A sensor for quantifying a widening reduction wear on a surface, comprising:
   a substrate comprising a surface with a wear starting position;
   a sensor element installed on an area of the substrate at a single level relative to the surface, wherein the sensor element comprises a proximal portion and a distal portion relative to the wear starting position; and
   an electrical measuring circuit connected to the sensor element;
   wherein the electrical measuring circuit measures an electrical characteristic of the sensor element that varies with a progressive reduction of the sensor element from the proximal portion to the distal portion of the sensor during a widening reduction wear of the surface from the wear starting position.

2. The sensor of claim 1, wherein the sensor element comprises a plurality of nested electrical conductor loops, wherein the widening reduction wear successively breaks the respective loops, changing an electrical characteristic of each loop in succession, and the electrical measuring circuit detects the electrical characteristic of each loop to quantify respective levels of wear of the surface.

3. The sensor of claim 2, wherein each electrical conductor loop comprises first and second rails and a rung between the rails, wherein the widening reduction wear successively breaks the rungs, changing the electrical characteristic of the sensor element in steps, which the electrical measuring circuit quantifies to indicate respective levels of wear of the surface.

4. The sensor of claim 3, wherein each rung has a zigzag shape.

5. The sensor of claim 1, wherein the sensor element comprises an electrically conductive ladder with first and second rails extending from proximate the wear starting position and a plurality of rungs between the rails, wherein the widening reduction wear successively breaks the rungs, changing the electrical characteristic in steps that the electrical measuring circuit quantifies to indicate respective levels of wear of the surface.

6. The sensor of claim 1, wherein the sensor element comprises a film of an electrically conductive material, wherein the widening reduction wear progressively reduces the film, changing the electrical characteristic thereof.

7. The sensor of claim 1, wherein the substrate surface is curved, and the sensor element is installed on the substrate surface.

8. The sensor of claim 1, wherein the substrate surface is curved, and the sensor element is installed at a single level in a coating on the substrate surface.

9. The sensor of claim 1, wherein the electrical measuring circuit communicates measurements of the electrical characteristic to a monitoring computer, and the monitoring computer calculates a wear depth based on a predetermined geometry of the widening reduction wear.

10. The sensor of claim 7, wherein:
the substrate forms a component in a gas turbine engine;
the monitoring computer comprises a memory and a clock;
an installation time is stored in the memory when the component is installed in the engine;
data is stored in the memory that defines an acceptable time series envelope for measurements of the electrical characteristic over time; and
the monitoring computer issues an alert if a measured electrical characteristic of the sensor at a given time after the installation time is not within the acceptable time series envelope.

11. A 2D sensor for quantifying a widening reduction wear on a surface, comprising:
a substrate comprising a surface with a wear starting position;
a 2D sensor element deposited on the surface, wherein the 2D sensor element comprises a proximal portion and a distal portion relative to the wear starting position; and
a means for correlating a change in an electrical characteristic of the 2D sensor element to a depth of wear in the surface.

12. The 2D sensor of claim 11, wherein the 2D sensor element comprises a plurality of nested electrical conductor loops and the means for correlating comprises an electrical measuring circuit, wherein widening reduction wear successively breaks the loops, changing an electrical characteristic of each loop in succession, and the electrical measuring circuit detects the changing electrical characteristic of each loop to quantify respective levels of wear of the surface.

13. The 2D sensor of claim 12, wherein each electrical conductor loop comprises first and second rails and a rung between the rails, wherein the widening reduction wear successively breaks the rungs, changing the electrical characteristic of the 2D sensor in steps that the electrical circuit quantifies to indicate respective levels of wear of the surface.

14. The 2D sensor of claim 13, wherein each rung has a zigzag shape.

15. The 2D sensor of claim 11, wherein the 2D sensor element comprises an electrically conductive ladder with first and second rails extending from the wear starting position and a plurality of rungs between the rails, wherein widening reduction wear successively breaks the rungs, changing an electrical characteristic of the 2D sensor element in steps that the means for correlating quantifies to indicate respective levels of wear of the surface.

16. The 2D sensor of claim 11, wherein the 2D sensor element comprises a film of an electrically conductive material, wherein widening reduction wear progressively reduces the film, changing the electrical characteristic thereof.

17. The 2D sensor of claim 11, wherein the substrate surface is curved, and the 2D sensor element is installed on the substrate surface.

18. The 2D sensor of claim 11, wherein the means for correlating comprises an electrical measuring circuit that communicates measurements of the electrical characteristic to a monitoring computer, and the monitoring computer calculates a wear depth based on a predetermined geometry of the widening reduction wear.

19. A sensor for quantifying a depth of wear on a curved surface of a spring clip in a gas turbine engine, comprising:
a spring clip comprising a surface with a wear starting position;
a 2D sensor element installed on an area of the spring clip, wherein the 2D sensor element comprises a proximal portion and a distal portion relative to the wear starting position; and
a measuring circuit connected to the 2D sensor element;
wherein the measuring circuit measures a characteristic of the 2D sensor element that varies with a progressive reduction of the 2D sensor element from the proximal portion toward the distal portion during wear of the spring clip surface;
wherein a change in the measured characteristic is correlated to a depth of the wear of the spring clip surface.

20. The sensor of claim 19, wherein the 2D sensor element comprises a surface pattern of an electrically conductive material, wherein the wear progressively reduces the surface pattern, producing progressive changes in the measured characteristic, and the measuring circuit quantifies the progressive changes to indicate the depth of wear of the spring clip surface.

* * * * *